United States Patent [19]

Panzera

[11] Patent Number: 4,481,036
[45] Date of Patent: Nov. 6, 1984

[54] GLAZE FOR USE ON NON-METALLIC DENTAL COPINGS

[75] Inventor: Carlino Panzera, Belle Mead, N.J.

[73] Assignee: Johnson & Johnson Dental Products Company, East Windsor, N.J.

[21] Appl. No.: 473,469

[22] Filed: Mar. 9, 1983

[51] Int. Cl.³ ............................................. C09K 3/00
[52] U.S. Cl. ..................................... 106/35; 433/199; 433/201; 433/202; 433/208; 501/66; 501/70
[58] Field of Search ...................... 501/66, 70; 106/35; 433/208, 209, 199, 202, 201

[56] References Cited

U.S. PATENT DOCUMENTS

| | | | |
|---|---|---|---|
| 2,000,285 | 5/1935 | Hoffmann | 106/6 |
| 2,897,595 | 8/1959 | Lee | 32/8 |
| 3,274,006 | 9/1966 | McKinnis | 501/66 |
| 3,423,829 | 1/1969 | Halpern et al. | 32/8 |
| 3,488,847 | 1/1970 | Pettrow | 32/8 |
| 3,504,437 | 4/1970 | Siegel | 32/8 |
| 3,902,881 | 9/1975 | Pirooz | 501/66 |
| 4,120,729 | 10/1978 | Smyth et al. | 106/35 |
| 4,281,991 | 8/1981 | Michl et al. | 433/202 |

Primary Examiner—Lorenzo B. Hayes
Attorney, Agent, or Firm—Charles J. Metz

[57] ABSTRACT

A stable glaze for use on ceramic dental copings has the following composition:

| Component | Proportion, % |
|---|---|
| $SiO_2$ | 71–74 |
| $Al_2O_3$ | 10–12 |
| $K_2O$ | 4–5 |
| $Na_2O$ | 4–5 |
| $CaO$ | 2–4.5 |
| $B_2O_3$ | 3.5–5.5 |

1 Claim, No Drawings

GLAZE FOR USE ON NON-METALLIC DENTAL COPINGS

The invention relates to a new family of dental porcelains having lower thermal expansion values than present commercial dental porcelains, and are thus useful for use with ceramic copings.

BACKGROUND OF THE INVENTION

Artificial dental crowns and bridges are usually made today using a metallic framework coated with a fused dental porcelain to provide the desired aesthetics. A number of new non-metallic materials are now appearing on the commercial market which are made of mixtures of ceramics, and which are recommended for use in making artificial dental crowns and, in some case, bridges. These materials have coefficients of thermal expansion much lower than existing dental alloys, for instance, $5-8 \times 10^{-6}$ versus $13-14 \times 10^{-6}$, per degree Celsius. Therefore, existing commercially available dental porcelain glazes cannot be used on the non-metallic copings to provide aesthetic properties since the thermal coefficients of expansion are too high.

This invention describes a new family of dental porcelains with lower thermal expansion values than commercial dental porcelain glazes, and therefore they match the expansion of the new ceramic copings. The new porcelains have the property of being easily modified by minor changes of composition to allow the thermal expansion properties to be changed, in order to match various copings. They also have the desirable property of being stable after repeated firings, in that their coefficients of thermal expansion and color shades remain essentially constant. This is particularly desirable in those cases wherein the glaze will have to be fired more than once. Such instances include those wherein several layers of glaze are used in order to obtain special effects (e.g., a different shade at the tip of the restoration than at the gingival area), and multi-unit bridges. It is another useful property of the glazes of the invention tha their maturing temperatures can be modified by minor compositional changes. This is desirable, for instance, in cases wherein several layers of glaze are used so that each successive layer matures at a slightly lower temperature.

SUMMARY OF THE INVENTION

The invention provides a translucent dental glaze composition suitable for application to dental ceramic copings, wherein the glazes have coefficients of thermal expansion of from about 4 to about $9 \times 10^{-6}$ in./in./°C., a firing temperature of from about 1700° to 1900° F., and which are composed of the following components:

TABLE I

| Component | Proportion, % |
|---|---|
| $SiO_2$ | 71-74 |
| $Al_2O_3$ | 10-12 |
| $K_2O$ | 4-5 |
| $Na_2O$ | 4-5 |
| $CaO$ | 2-4.5 |
| $B_2O_3$ | 3.5-5.5 |

These translucent dental glazes have the desirable property of being stable upon repeated firings at temperaures up to about 1900° F.

DETAILED DESCRIPTION OF THE INVENTION

The translucent glaze composition of this invention can be prepared by melting together sufficient precursor components to yield the composition shown above in the table. Suitable precursors include silica, alumina, boric acid, felspar, calcium carbonate, sodium carbonate, potassium carbonate, or if desired, the actual oxides, blended in proportion to yield the appropriate ratios shown in the above table.

The preparation of such materials is well known in the art. After the materials are blended, preferably in finely divided powder form such as powder sufficiently fine to pass through a 200 mesh screen (Tyler series), the precursors are heated to a temperature of at least 2100° F., up to 2300° F., and higher, in a crucible to form a glass. The molten glass may then be quenched in water, dried, and ground in a ball mill, to provide the glaze material of the invention in the form of a powder. It is preferred that the powder be ground finely enough so tht it will pass through a 160 mesh screen (Tyler series).

The properties of the glaze may be adjusted by applying the following principles:

Within the ranges of component proportions set forth above in Table I, the coefficient of thermal expansion can be increased by decreasing the proportion of $SiO_2$ and/or $B_2O_3$, and/or by increasing the proportion of the alkali metal oxides. The fusion point can be reduced by increasing the proportion of $B_2O_3$, $CaO$ and/or the alkali metal oxides. As between the two alkali metal oxides, an increase in the $Na_2O:K_2O$ ratio lowers the fusion point. It is well within the skill of the ceramics art to apply these principles to make fine adjustments to the thermal expansion coefficients and fusion temperatures.

Other materials can be employed in the glazes of the invention. For instance, $MgO$ and/or $BaO$ can be used in place of some of the $CaO$. Some $Li_2O$ can be used in place of some of the $Na_2O$ and/or $K_2O$, especially if fusion point reduction is desired. Small amounts of zirconia and zinc oxide can be added to th glaze. And conventional pigments can be added in small amounts (usually less than one weight per cent) to tint the glaze. Such pigments include transition metal compounds such as vanadates, manganates, and chromates.

The following Examples illustrate the invention:

EXAMPLES 1 and 2

Glazes were made having the compositions set forth below in Table II from silica, tabular grade alumina, potassium carbonate, sodium carbonate, calcium carbonate, and boric acid. The raw materials were blended, ball milled for two hours, and then transferred to a dense alumina crucible. The charge was then fired to 1400° C. and held for 4 hours, quenched in water, crushed, and then ball milled to a powder that passes through a 160 mesh screen (Tyler series).

Thermal expansion test bars where made by pressing 5 grams of powder into a bar $\frac{1}{4} \times \frac{1}{4} \times 2$ inches in dimension, and then firing to the maturing temperature indicated below in Table II. The firing rate was 90° to 100° F. per minute.

The thermal expansion stability of the bars to repeated firings was treated by the following procedure:

Ten heating cycles were used. Cycle Nos. 1, 4, 7, and 10 were carried out at a 5° C. per minute heat-up rate up to 575° C. The other cycles were carried out at a 90° to 100° F. heat-up rate to the maturing temperature. After these 10 heating cycles, no significant change in the coefficients of thermal expansion of the bars of Examples 1 and 2 was noted.

In order to evaluate the color stability of the glazes, 1½ inch diameter disks were pressed from 7 grams of powder, and were fired under the same conditions as the bars. The disks were then subjected to four heating cycles at a heat-up rate of 90° to 100° F. per minute heat-up rate to the maturing temperature. No color change was noted after these four cycles. (The color was measured by an Applied Color Systems color computer, Model 500).

Table II displays the compositions, maturing temperatures, and the coefficients of thermal expansion for Examples 1 and 2.

TABLE II

|  | Example 1 | Example 2 |
|---|---|---|
| $SiO_2$ | 72.5 | 72.5 |
| $Al_2O_3$ | 11.2 | 10.2 |
| $K_2O$ | 4.5 | 4.5 |
| $Na_2O$ | 4.5 | 4.5 |
| CaO | 2.8 | 3.8 |
| $B_2O_3$ | 4.5 | 4.5 |
| Maturing Temp. - °F. | 1825 | 1800 |
| Coeff. of T.E., ($\times 10^6$ in./in./°C.) | 5.3 | 5.5 |

What is claimed is:

1. A translucent dental glaze composition suitable for application to a dental porcelain ceramic substrate, said glaze having a maturing temperature of from about 1700° to about 1900° F., and a coefficient of thermal expansion of from about 4 to about $9 \times 10^{-6}$ in./in./°C., and consisting of, on a weight basis, the following components:

| Component | Proportion, % |
|---|---|
| $SiO_2$ | 71-74 |
| $Al_2O_3$ | 10-12 |
| $K_2O$ | 4-5 |
| $Na_2O$ | 4-5 |
| CaO | 2-4.5 |
| $B_2O_3$ | 3.5-5.5 |

* * * * *